United States Patent [19]

Belkin et al.

[11] Patent Number: 5,620,435

[45] Date of Patent: Apr. 15, 1997

[54] EYE SURGERY

[75] Inventors: Michael Belkin, Givat Shmuel; Abraham Katzir, Tel Aviv; Alon Goldring, Jerusalem; Alex Harel, Savion; Yeshayahu S. Eisenberg, Kiryat Tivon, all of Israel

[73] Assignees: Optomedic Medical Technologies, Ltd., Or-Yehuda; Ramot University Authority for Applied Research, Tel-Aviv, both of Israel

[21] Appl. No.: 539,246

[22] Filed: Oct. 5, 1995

[51] Int. Cl.$^6$ .................................................. A61N 5/06
[52] U.S. Cl. .................................................. 606/4; 606/3
[58] Field of Search ................................ 606/4, 5, 6, 10, 606/11, 12

[56] References Cited

U.S. PATENT DOCUMENTS

| 3,971,382 | 7/1976 | Krasnov | 606/6 |
| 4,672,969 | 6/1987 | Dew | 606/16 |
| 5,246,435 | 9/1993 | Bille et al. | 606/6 |
| 5,290,272 | 3/1994 | Burstein et al. | 606/4 |

OTHER PUBLICATIONS

Keates, R.H., "Carbon Dioxide Laser Use in Wound Sealing and Epikeratophakia", *Journal of Cataract & Refractive Surgery*, vol. 13, May 1987, pp. 290–295.

Fukutake, T., "Laser Surgery for Allergic Rhinitis", *Arch. of Otolaryngol Head and Neck Surgery*, vol. 112, Dec. 1986, pp. 1280–1282.

Boyd, B.F., "Valuable New Findings on Pathophysiology of Cataract Surgery", *Highlights of Ophthalmology Letter*, vol.XXI, No. 9, 1993 Series, pp. 10–15.

Blumenthal, M., "Lens Anatomical Principles and their Technical Implications in Cataract Surgery", *J. of Cataract and Refractive Surgery*, vol. 17, Mar. 1991, pp. 205–210.

Wilson, M.E., "Comparison of Mechanized Anterior Capsulectomy and Manual Continuous Capsulorhexis in Pediatric Eyes", *J. of Cataract and Refractive Surgery*, vol.20, Nov. 1994, pp. 602–606.

Gailitis, R.P., "Laser Welding of Synthetic Epikeratoplasty Lenticules to the Cornea"*Refractive and Corneal Surgery*, vol. 6, Nov.–Dec. 1990, pp. 430–436.

*Primary Examiner*—Angela D. Sykes
*Assistant Examiner*—Sonya Harris-Ogugua
*Attorney, Agent, or Firm*—Helfgott & Karas, P.C.

[57] ABSTRACT

A method for welding ocular tissues to each other including providing a first portion of ocular tissue having a leading edge and a second portion of ocular tissue having a leading edge, positioning the leading edge of the first portion of ocular tissue directly adjacent to and against the leading edge of the second portion of ocular tissue, and applying pulses of a laser light from a source thereof substantially simultaneously to the leading edge of the first portion of ocular tissue and to the leading edge of the second portion of ocular tissue, the pulses of the laser light penetrating the portions of ocular tissue to a depth of approximately 1–300 microns so that the leading edge of the first portion of ocular tissue may be securely welded to the leading edge of the second portion of ocular tissue, the laser light having a wavelength of approximately 10.6 microns and a power output level sufficient to maintain the portions of ocular tissue at a temperature of approximately 45–60 degrees Celsius during the applying of the laser light.

10 Claims, 3 Drawing Sheets

EYE SURGERY

FIELD OF THE INVENTION

The present invention relates to methods for ophthalmic laser surgery generally.

BACKGROUND OF THE INVENTION

The use of laser light in ophthalmic surgery is extensive. Laser light may be used to join or cut ocular tissues.

The use of laser light to join or weld ocular tissues, such as corneal and scleral tissues, is well known. U.S. Pat. No. 5,290,272 issued to Burstein et al describes a method for joining ocular tissues with laser light having a wavelength in the range of 1400–1900 nm or 2100–2400 nm, and in which the depth of penetration in the tissue is about 0.2–2.0 mm.

The selection of the wavelength is critical, inter alia, for proper penetration of the ocular tissue. Too short a wavelength results in the laser energy not being absorbed as desired in the tissue. The laser energy instead may penetrate the tissue too deeply, thus endangering the lens and the retina. Too long a wavelength results in the laser energy penetrating to a relatively shallow depth in the tissue, resulting in a weak weld.

Burstein et al clearly teach that a carbon dioxide laser, whose wavelength is about 10,600 nm, is not suitable for welding ocular tissue. The failure of carbon dioxide laser light to produce effective welds in ocular tissues is also discussed in other publications, such as R. H. Keates et al, "Carbon dioxide laser use in wound sealing and epikeratophakia", J. Cataract Refract. Surg., 13:290–295 (1987) and R. P. Gallitis, "Laser Welding of Synthetic Epikeratoplasty Lenticules to the Cornea", Refractive and Corneal Surgery, 6:430–436 (1990). Both of these publications report undesirable tissue damage and shrinkage when using a carbon dioxide laser.

However, in general, carbon dioxide lasers are very useful for many surgical operations, as is known in the art, and some are used in ophthalmic surgery as well, such as in lid surgery. It is therefore desirable to overcome the abovementioned drawbacks and to find a method for using carbon dioxide lasers for joining ocular tissue.

The use of laser light to cut ocular tissue is also well known, particularly in extracapsular cataract extraction. Extracapsular cataract extraction is the removal of an opaque lens through the anterior segment of the eye, leaving the capsule which surrounds the lens intact. The opaque lens is replaced by an intraocular lens (IOL), usually placed inside the capsule.

A critical step of extracapsular cataract extraction and intraocular lens implantation is anterior capsulotomy. Anterior capsulotomy is the surgical cutting and removal of a portion of the anterior capsule in order to allow removal of the opaque lens while preserving most of the lens capsule which serves as a barrier for the vitreous of the eye and a support for the implanted intraocular lens.

Traditional surgical techniques used in anterior capsulotomy often are associated with extension of radial tears to the periphery of the capsule. This results frequently in asymmetric fixation of the IOL and numerous other complications, including IOL decentration and inflammatory reaction caused by the contact between the foreign lens material and the delicate uveal tissue.

Since 1986 a new technique has been promoted as the preferred type capsulectomy, namely "continuous curvilinear capsulorhexis" (CCC). The CCC technique generally involves puncturing the anterior lens capsule ("capsulorhexis") at a distance from the center of the visual axis and then cutting a continuous curvilinear central opening for removal of the lens. The round and intact margin of the central opening is meant to assure a consistent, safe and secure placement of the IOL within the capsule. Since the introduction of the CCC technique, the rate of IOL related complications has been reduced and smaller and safer IOL's have been developed.

Anterior capsulectomy and the CCC technique are discussed in various publications, such as M. E. Wilson et al, "Comparison of mechanized anterior capsulectomy and manual continuous capsulorhexis in pediatric eyes", J. Cataract Refract. Surg., 20:602–606 (1994), B. F. Boyd, "Valuable new findings on pathophysiology of cataract/IOL surgery", Highlights of Ophthalmology Letter, Vol. XXI, No. 9, pp. 10–15 (1993) and M. Blumenthal et al, "Lens anatomical principles and their technical implications in cataract surgery, Part I: The lens capsule", J. Cataract Refract. Surg., 17:205–210.

In general, the CCC technique requires manual dexterity and delicate instruments, such as manually using a bent needle (cystotome) or a special capsule forceps.

SUMMARY OF THE INVENTION

The present invention seeks to provide a method for joining ocular tissue with pulsed carbon dioxide laser light. In addition, the present invention seeks to provide a method for performing anterior capsulotomy with pulsed carbon dioxide laser light.

The present inventors have found that a pulsed carbon dioxide laser device with an output in the range of 300–4000 mW and a pulse duration in the range of 2000–1 msec, provides a tissue penetration depth of about 1–300 microns and succeeds in welding ocular tissue with substantially no tissue damage or shrinkage. Any combination of corneal and scleral tissue may be welded, and the method is applicable for joining tissues which have been separated either by surgical or traumatic incisions.

The method of the present invention for joining ocular tissue is applicable for other ophthalmic surgical procedures, such as cataract extraction, corneal transplant, trauma surgery, retina and extraocular muscles surgery and keratomileusis.

With the addition of a suitable attachment, the same pulsed carbon dioxide laser device used for joining ocular tissue may be used for creating an opening in the anterior capsule for use in CCC. The attachment to the pulsed carbon dioxide laser device is preferably a metallic probe in which the laser beam is reflected at a distal end of the probe. The laser beam is reflected, inter alia, to permit insertion of a sufficiently slender probe into the eye and still provide correctly oriented cutting of the capsule by the reflected laser beam.

When performing CCC, the probe is inserted into the anterior chamber and the reflected laser beam pulses are used to cut a plurality of discrete and contiguous circular cuts, preferably 1.0–1.5 mm in diameter, the cuts together forming a generally circular opening on the anterior capsule, preferably 5–7 mm in diameter. The anterior capsulotomy is performed quickly, accurately and without exerting pressure on the capsule and without risk of extension of the tear to the periphery of the lens. The probe which transmits the carbon dioxide beam into the eye is preferably thin (preferably not more than 1 mm in diameter, although may be from about 0.5 to 1.5 mm in diameter), so that it does not touch delicate ocular tissue.

There is thus provided in accordance with a preferred embodiment of the present invention, a method for welding ocular tissues to each other, or welding the tissues at their respective positions at the time of surgery, including:

providing a first portion of ocular tissue having a leading edge and a second portion of ocular tissue having a leading edge;

positioning the leading edge of the first portion of ocular tissue directly adjacent to and against the leading edge of the second portion of ocular tissue; and applying pulses of a laser light from a source thereof substantially simultaneously to the leading edge of the first portion of ocular tissue and to the leading edge of the second portion of ocular tissue, the pulses of the laser light penetrating the portions of ocular tissue to a depth of approximately 1–300 microns so that the leading edge of the first portion of ocular tissue may be securely welded to the leading edge of the second portion of ocular tissue, the laser light having a wavelength of approximately 10.6 microns and a power output level sufficient to maintain the portions of ocular tissue at a temperature of approximately 45–60 degrees Celsius during application of the laser light.

The method may be used to weld corneal tissue to corneal tissue, scleral tissue to scleral tissue, or corneal tissue to scleral tissue.

In accordance with a preferred embodiment of the present invention, the power output level is approximately in the range of 300–4000 mW. Preferably, the pulses have a duration in the range of approximately 2000–1 msec.

There is also provided in accordance with a preferred embodiment of the present invention, a method for performing anterior capsulotomy including applying pulses of a laser light from a source thereof on a portion of the anterior capsule, thereby creating a plurality of discrete and contiguous cuts, the cuts together forming an opening on the anterior capsule.

In accordance with a preferred embodiment of the present invention, the laser light has a wavelength of approximately 10.6 microns.

Preferably, the discrete and contiguous cuts are circular, and are 0.5–1.5 mm in diameter. Preferably the opening is generally circular and is 5–7 mm in diameter.

BRIEF DESCRIPTION OF THE DRAWINGS

The present invention will be understood and appreciated from the following detailed description, taken in conjunction with the drawings in which.

DETAILED DESCRIPTION OF PREFERRED EMBODIMENTS

Figure 1:
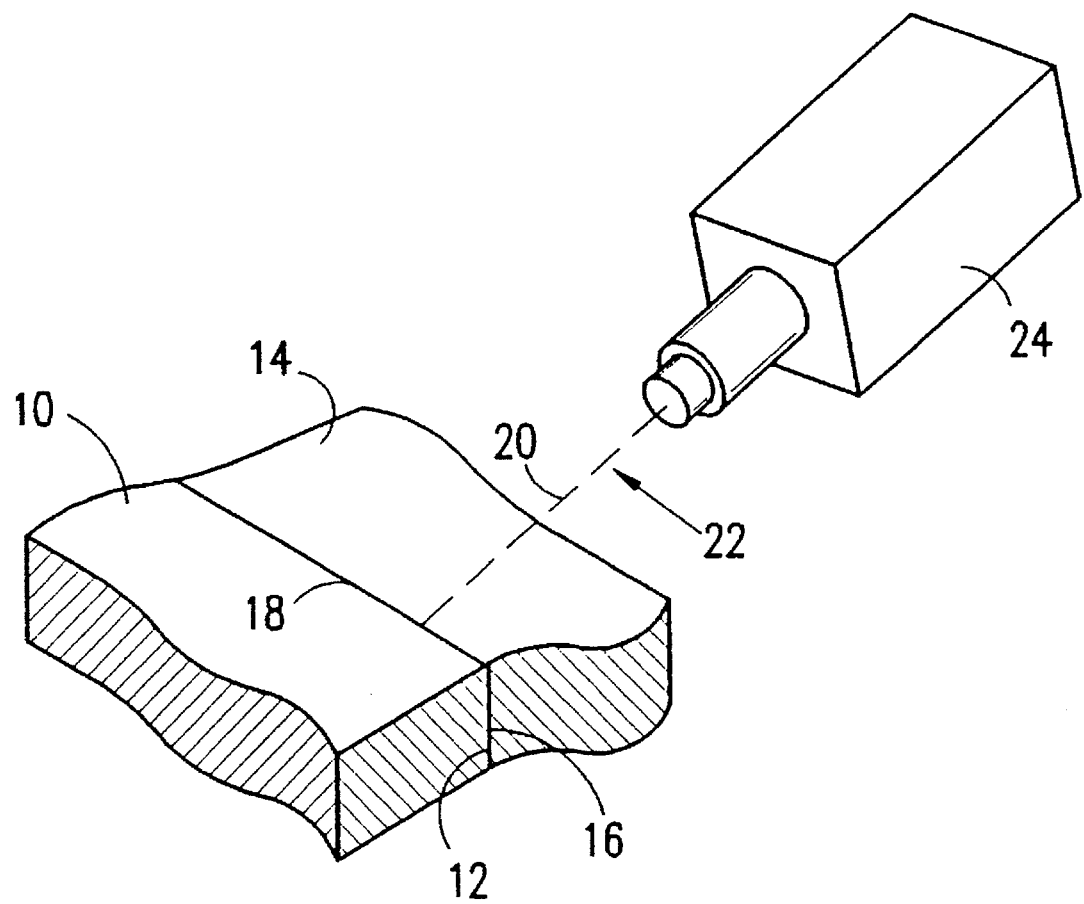
FIG. 1 is a simplified illustration of a method of welding ocular tissues to each other in accordance with a preferred embodiment of the present invention.

Reference is now made to FIG. 1 which illustrates a method of joining ocular tissues to each other in accordance with a preferred embodiment of the present invention. A first portion 10 of ocular tissue having a leading edge 12 and a second portion 14 of ocular tissue having a leading edge 16 are provided. Portions 10 and 14 of ocular tissue may be either corneal or scleral tissue and may have been separated from each other by surgical or traumatic incisions.

Leading edge 12 is positioned directly adjacent to and against leading edge 16 such that a weldable seam 18 is provided with substantially no gaps or irregularities which could hinder formation of a secure weld.

Pulses 20 of a laser light 22 from a laser light source 24 are then applied substantially simultaneously to leading edges 12 and 16. The laser light 22 has a wavelength of approximately 10.6 microns. Laser light source 24 is preferably a carbon dioxide pulsed laser device, such as Kaplan Pendulaser 115 manufactured by Optomedic Medical Technologies Ltd., Or-Yehuda, Israel.

The power output level of laser light 22 is preferably in the range of about 300–4000 mW. Pulses 20 preferably have a duration of about 2000–1 msec, the 2000 msec duration corresponding to a power output level of about 300 mW, and the 1 msec duration corresponding to a power output level of about 4000 mW. Such an application of pulses 20 of laser light 22 typically penetrates portions 10 and 14 of ocular tissue to a depth of about 1–300 microns, thereby forming a secure weld.

The method of the present invention for joining ocular tissue is applicable for a variety of ophthalmic surgical procedures, such as cataract extraction, corneal transplant, trauma surgery, retina and extraocular muscles surgery and keratomileusis.

Figure 2:
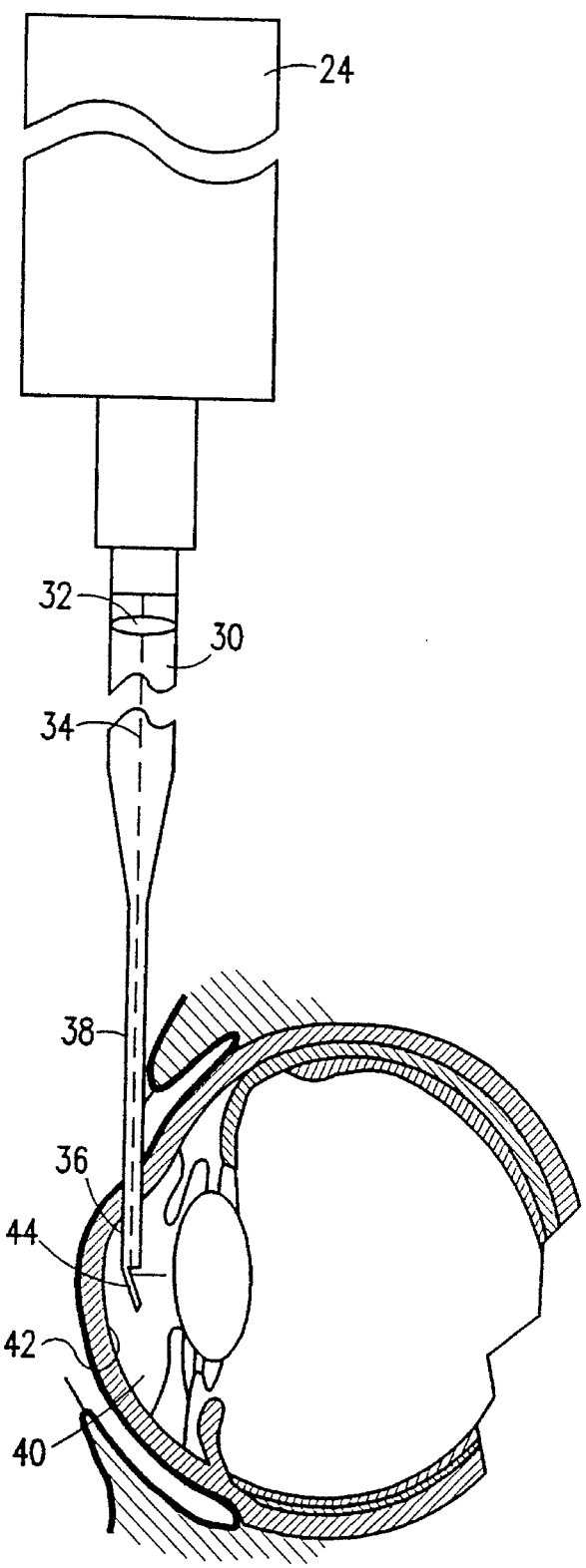
FIG. 2 is a simplified illustration of a probe inserted into the anterior chamber of an eye and useful in a method of performing anterior capsulotomy in accordance with a preferred embodiment of the present invention.

Reference is now made to FIG. 2 which illustrates a method for performing anterior capsulotomy, in accordance with a preferred embodiment of the present invention.

Laser light source 24 is preferably attached to a handpiece 30. Preferably a lens 32 directs pulses 34 of laser light to a distal end 36 of a hollow probe 38. Probe 38 is preferably slender, about 0.5–1.5 mm in diameter, although preferably not more than 1 mm in diameter, so that it may be inserted into the anterior chamber 40 of the eye and not touch the corneal endothelium 42 during capsulorhexis.

Located at distal end 36 of probe 38 is a reflective portion 44 which is configured to reflect pulses 34 of laser light on to the anterior lens capsule for performing anterior capsulotomy.

Figure 3:
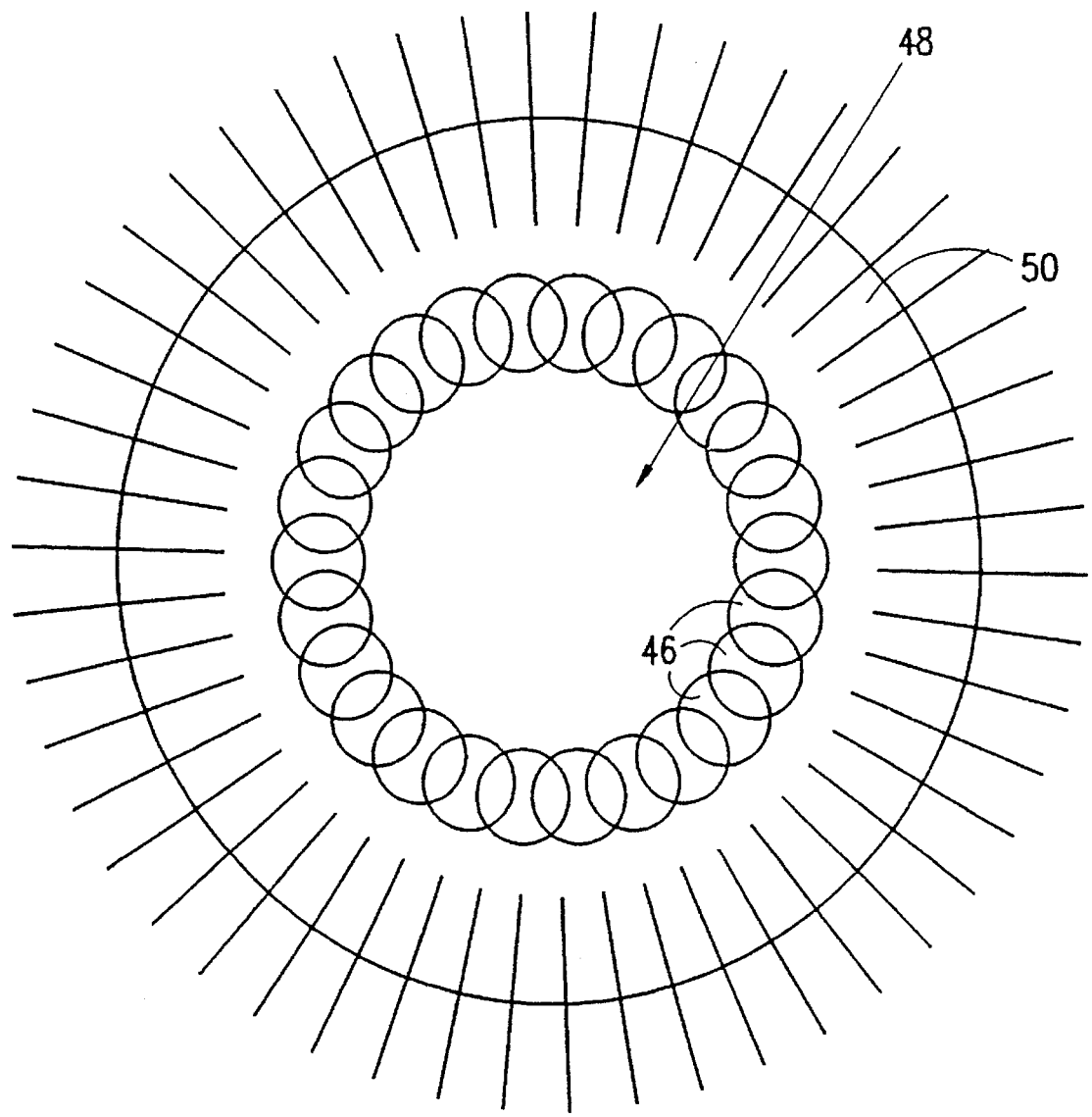
FIG. 3 is a simplified illustration of a plurality of discrete and contiguous cuts, formed on the anterior capsule of the eye in accordance with a preferred embodiment of the present invention.

Reference is now made to FIG. 3 which illustrates an example of anterior capsulotomy using probe 38 shown in FIG. 2. The laser beam pulses reflected by portion 44 (shown in FIG. 2) are used to cut a plurality of discrete and contiguous cuts 46, preferably, although not necessarily, circular and 0.5–1.5 mm in diameter. Cuts 46 together form an opening 48 on the anterior capsule 50. Opening 48 is preferably circular and 5–7 mm in diameter. As is known in the art, opening 48 may alternatively be of any generally curvilinear shape, such as, for example, oval, cordate or undulate. The anterior capsulotomy is performed quickly, accurately and without exerting pressure on capsule 50 and without jaggedness and risk of extension of the tear to the periphery of the lens.

It will be appreciated by persons skilled in the art that the present invention is not limited to what has been particularly shown and described hereinabove. Rather, the scope of the present invention is defined only by the claims that follow:

We claim:

1. A method for welding a first portion of ocular tissue having a leading edge to a second portion of ocular tissue having a leading edge, said method comprising the steps of:

positioning said leading edge of said first portion of ocular tissue directly adjacent to and against said leading edge of said second portion of ocular tissue; and applying pulses of a laser light from a source thereof substantially simultaneously to said leading edge of said first portion of ocular tissue and to said leading edge of said second portion of ocular tissue, in a pulsed mode, wherein multiple pulses impinge on a given location, said pulses of said laser light penetrating said portions of ocular tissue to a depth of approximately 1–300 microns so that said leading edge of said first portion of ocular tissue may be securely welded to said leading edge of said second portion of ocular tissue, said laser light having a wavelength of approximately 10.6 microns and a power output level sufficient to maintain said portions of ocular tissue at a temperature of approximately 45–60 degrees Celsius during said applying of said laser light.

2. A method according to claim 1 and wherein said first portion of ocular tissue is comprised of corneal tissue and said second portion of ocular tissue is comprised of corneal tissue.

3. A method according to claim 1 and wherein said first portion of ocular tissue is comprised of scleral tissue and said second portion of ocular tissue is comprised of scleral tissue.

4. A method according to claim 1 and wherein said first portion of ocular tissue is comprised of corneal tissue and said second portion of ocular tissue is comprised of scleral tissue.

5. A method according to claim 1 and wherein said power output level is approximately in the range of 300 mW increasing to 4000 mW, and wherein said pulses have a duration which correspondingly decreases from approximately 2000 msec to 1 msec.

6. A method for performing an anterior capsulotomy including applying pulses of a laser light from a source thereof on a portion of the anterior capsule of an eye lens, thereby creating a plurality of discrete and contiguous cuts, said cuts together releasing part of said anterior capsule, and wherein said laser light has a wavelength of approximately 10.6 microns.

7. A method according to claim 6 and wherein said discrete and contiguous cuts are circular.

8. A method according to claim 6 and wherein said discrete and contiguous cuts are circular and are 0.5–1.5 mm in diameter.

9. A method according to claim 6 and wherein said opening is generally circular.

10. A method according to claim 6 and wherein said opening is generally circular and is 5–7 mm in diameter.

* * * * *